United States Patent [19]
Pomeranz et al.

[11] Patent Number: 6,014,579
[45] Date of Patent: Jan. 11, 2000

[54] ENDOCARDIAL MAPPING CATHETER WITH MOVABLE ELECTRODE

[75] Inventors: Mark L. Pomeranz, Los Gatos; Susan M. Pietroski, Menlo Park; Harold A. Heitzmann, Cupertino; Robert F. Bencini, Sunnyvale; Edward M. Gillis, Mountain View, all of Calif.

[73] Assignee: Cardiac Pathways Corp., Sunnyvale, Calif.

[21] Appl. No.: 08/897,657

[22] Filed: Jul. 21, 1997

[51] Int. Cl.[7] .............................. A61B 5/0408; A61N 1/05
[52] U.S. Cl. .............................. 600/374; 607/122; 606/41
[58] Field of Search .................................. 600/372–381; 606/41, 46; 607/116, 119, 122, 125, 126

[56] References Cited

U.S. PATENT DOCUMENTS

| | | |
|---|---|---|
| 5,156,151 | 10/1992 | Imran . |
| 5,254,088 | 10/1993 | Lundquist . |
| 5,255,679 | 10/1993 | Imran ...................................... 128/642 |
| 5,324,284 | 6/1994 | Imran ...................................... 606/15 |
| 5,348,554 | 9/1994 | Imran et al. ............................... 606/41 |
| 5,395,327 | 3/1995 | Lundquist . |
| 5,397,321 | 3/1995 | Houser . |
| 5,400,783 | 3/1995 | Pomeranz et al. . |
| 5,409,000 | 4/1995 | Imran ...................................... 128/642 |
| 5,476,495 | 12/1995 | Kordis et al. . |
| 5,531,686 | 7/1996 | Lundquist . |
| 5,558,073 | 9/1996 | Pomeranz et al. ....................... 128/642 |
| 5,595,183 | 1/1997 | Swanson et al. . |
| 5,598,848 | 2/1997 | Swanson et al. . |
| 5,636,634 | 6/1997 | Kordis et al. . |
| 5,680,860 | 10/1997 | Imran ...................................... 128/642 |
| 5,836,947 | 11/1998 | Fleischman et al. ..................... 606/47 |

*Primary Examiner*—Lee Cohen
*Assistant Examiner*—David M. Ruddy
*Attorney, Agent, or Firm*—Flehr Hohbach Test Albritton & Herbert LLP

[57] ABSTRACT

An endocardial mapping catheter for introduction into a chamber of a heart formed by a wall. The flexible elongate tubular member has proximal and distal extremities and extends along a longitudinal axis. A plurality of longitudinally-extending spaced-apart members are carried by the distal extremity of the flexible elongate tubular member and have proximal extremities and interconnected distal extremities. Certain of the plurality of longitudinally-extending members are arms of a basket-like assembly and are movable between contracted positions and expanded positions in which the arms bow outwardly from the longitudinal axis. A plurality of longitudinally spaced-apart electrodes are carried by each of the arms. Electrical conductors extend through the flexible elongate tubular member and are connected to the electrodes for performing electrical functions with respect to the electrodes. At least one additional electrode is slidably mounted on one of the longitudinally-extending members.

14 Claims, 5 Drawing Sheets

ENDOCARDIAL MAPPING CATHETER WITH MOVABLE ELECTRODE

FIELD OF THE INVENTION

This invention relates generally to endocardial mapping catheters and, more particularly, to endocardial mapping catheters with movable electrodes.

BACKGROUND OF THE INVENTION

Endocardial mapping catheters have heretofore been provided. See, for example, U.S. Pat. No. 5,156,151 to Imran. Movable electrodes have been provided for use therewith. U.S. Pat. No. 5,400,783 to Pomerariz et al., for example, discloses a plurality of movable electrodes mounted on an arm swingably disposed within a basket assembly. U.S. Pat. No. 5,324,284 discloses an endocardial mapping system utilizing a separately controlled ablation catheter. See also U.S. Pat. No. 5,476,495 to Kordis et al. It has been found that endocardial mapping catheters having other types of movable electrodes would be desirable.

SUMMARY OF THE INVENTION

Accordingly, it is a general object of the present invention to provide a new and improved endocardial mapping catheter with a movable electrode.

Another object of the invention is to provide an endocardial mapping catheter of the above character in which the movable electrode is an ablation electrode carried within a basket-like assembly and having a diameter which is large relative to the diameter of the catheter shaft on which the ablation electrode is mounted.

Another object of the invention is to provide an endocardial mapping catheter of the above character in which the ablation electrode has a diameter which is large relative to the diameter of the lumen in the catheter shaft of the basket-like assembly in which the ablation catheter shaft is disposed.

Another object of the invention is to provide an endocardial mapping catheter of the above character in which the movable electrode is a saline electrode.

Another object of the invention is to provide an endocardial mapping catheter of the above character in which the movable electrode is slidably disposed on a basket-like assembly.

Another object of the invention is to provide an endocardial mapping catheter of the above character in which the movable electrode is slidably disposed on an arm rotatably mounted within the basket-like assembly.

Another object of the invention is to provide an endocardial mapping catheter of the above character in which the movable electrode is slidably disposed on a pull wire of a basket-like assembly.

Another object of the invention is to provide an endocardial mapping catheter of the above character in which the movable electrode is cantilevered from the pull wire so as to be positionable between the arms of the basket-like assembly.

Another object of the invention is to provide an endocardial mapping catheter of the above character in which the movable electrode can be directed in first and second opposite directions by means of a push/pull wire.

Additional objects and features of the invention will appear from the following description in which the preferred embodiments are set forth in detail in conjunction with the accompanying drawings.

DETAILED DESCRIPTION OF PREFERRED EMBODIMENTS

In general, an endocardial mapping catheter for introduction into a chamber of a heart formed by a wall is provided.

The flexible elongate tubular member has proximal and distal extremities and extends along a longitudinal axis. A plurality of longitudinally-extending spaced-apart members are carried by the distal extremity of the flexible elongate tubular member and have proximal and distal extremities. Means is provided for interconnecting the distal extremities of the longitudinally-extending members. Certain of the plurality of longitudinally-extending members are arms of a basket-like assembly and are movable between contracted positions and expanded positions in which the arms bow outwardly from the longitudinal axis. A plurality of longitudinally spaced-apart electrodes are carried by each of the arms. Electrical means extends through the flexible elongate tubular member and is connected to the electrodes for performing electrical functions with respect to the electrodes. At least one additional electrode and means for slidably mounting the additional electrode on one of the longitudinally-extending members are provided.

More in particular, an endocardial mapping catheter 31 is shown in FIGS. 1–7 and includes a flexible elongate tubular member or catheter shaft 32 made from any suitable material such as plastic. Shaft 32 has an external size ranging from 5 to 11 French. Catheter shaft 32 has proximal and distal extremities 32a and 32b and length so that when the distal extremity is inside a chamber of the heart the proximal extremity is outside of the body. The catheter shaft 32 extends along a central longitudinal axis 33 and is provided with at least one lumen in the form of central passageway 36 extending between extremities 32a and 32b of the catheter shaft and having an internal diameter of approximately 0.045 inch. The catheter shaft 32 can have a metal braid (not shown) or other reinforcing member for providing torsional rigidity to the catheter shaft.

Figures 1, 2, 3, 4, 5, 6, 7:
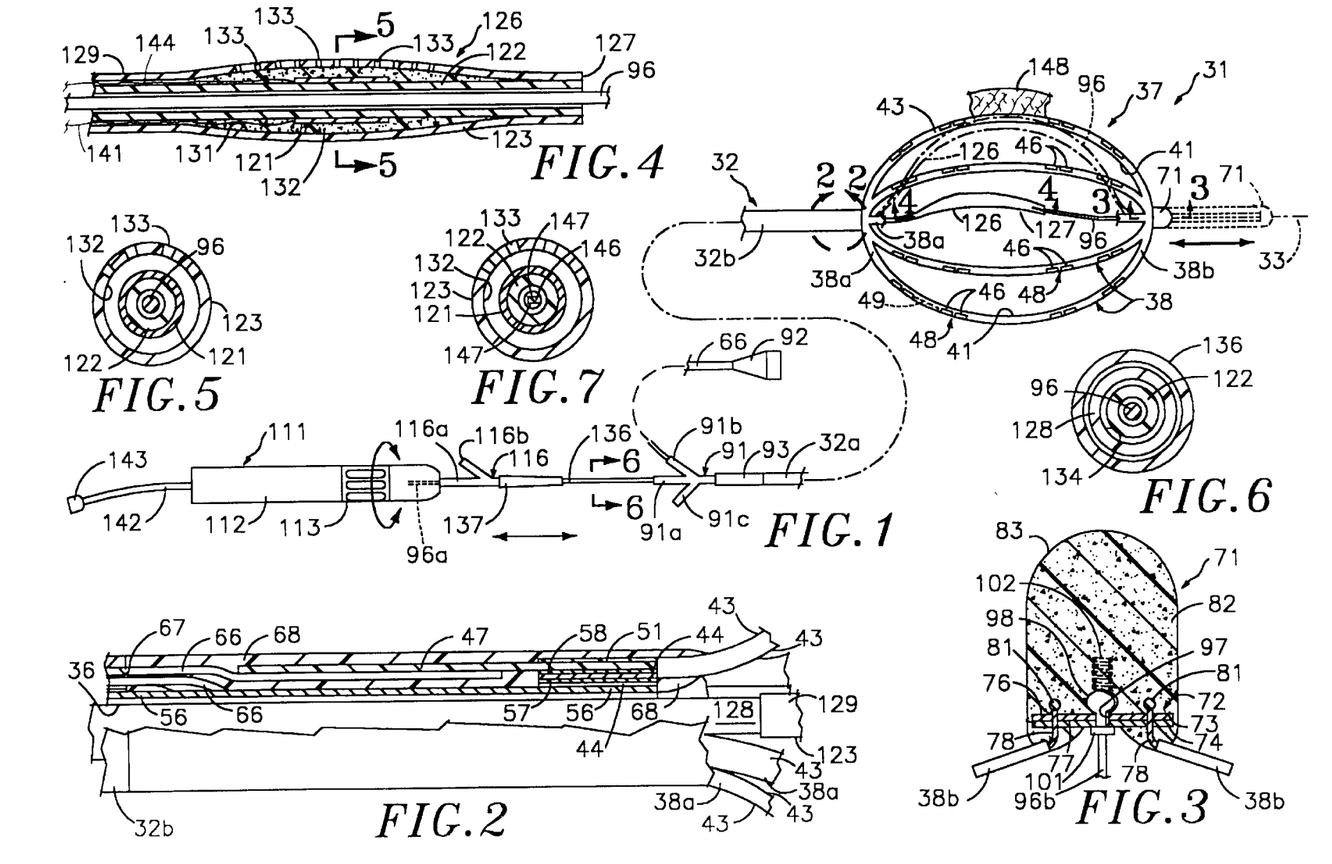
FIG. 1 is a side elevational view, partially cut away, of an embodiment of the endocardial mapping catheter with movable electrode of the present invention.
FIG. 2 is an enlarged side elevational view, partially sectioned, of the catheter of FIG. 1 taken along the line 2—2 of FIG. 1.
FIG. 3 is a cross-sectional view of the catheter of FIG. 1 taken along the line 3—3 of FIG. 1.
FIG. 4 is a cross-sectional view of the movable electrode of the catheter of FIG. 1 taken along the line 4—4 of FIG. 1.
FIG. 5 is a cross-sectional view of the movable electrode of the catheter of FIG. 1 taken along the line 5—5 of FIG. 4.
FIG. 6 is a cross-sectional view of the catheter of FIG. 1 taken along the line 6—6 of FIG. 1.
FIG. 7 is a cross-sectional view, similar to FIG. 5, of an alternate embodiment of the catheter of FIG. 1.

An expandable means is carried by distal extremity 32b of catheter shaft 32 and is formed from a plurality of longitudinally-extending spaced-apart members (see FIGS. 1 and 2). The expandable means includes a basket-like assembly or basket assembly 37 having a plurality of eight elongate members or arms 38 with proximal and distal extremities 38a and 38b. Basket assembly 37 is movable between a first or contracted position shown partially in dashed lines in FIG. 1, in which the basket assembly is adapted to pass through a vessel of the body into a chamber of the heart, and a second or expanded position shown in solid lines in FIG. 1, in which basket arms 38 bow outwardly relative to longitudinal axis 33 so as to engage the inside of the wall of the heart. Arms 38 are circumferentially spaced-apart about axis 33 at approximately 45° angles so as to be symmetrically positioned. Spaces 41 are provided between arms 38 for permitting blood to flow through basket assembly 37 while it is in its expanded position in the heart.

As more specifically described in copending U.S. patent application Ser. No. 08/555,927 filed Nov. 13, 1995, incorporated herein by this reference, each arm 38 is generally strip-like in conformation and has opposite inner and outer generally parallel surfaces 43 (see FIGS. 1 and 2). Each arm 38 includes a flexible elongate support member or strip 44 made from any suitable material such as Nitinol or another superelastic shape memory alloy and is provided with a predetermined bowed shape. A plurality of electrodes 46 are carried by basket assembly 37 in longitudinally and radially spaced-apart positions along the arms 38. In this regard, each arm 38 has a flex strip 47 with a plurality of eight electrodes 46 in longitudinally spaced-apart positions thereon. The eight electrodes on each arm 38 are grouped in four pairs so as to provide a plurality of four longitudinally spaced-apart electrode pairs 48 as shown in FIG. 1. The flex strip 47 in each arm 38 further includes a plurality of electrical or lead means in the form of conductive traces 49 which extend longitudinally along the flex strip. Traeces 49, a portion of one of which is shown in dashed lines in FIG. 1, are electrically connected to electrodes 46. An encapsulating PET sleeve 51 is heat shrunk around the flex strip 47 and other interior components of arms 38.

Means is included within probe 31 for securing proximal extremities 38a of arms 38 in circumferentially spaced-apart positions about distal extremity 32b of catheter shaft 32 (see FIG. 2). In this regard, and as more fully described in U.S. patent application Ser. No. 08/555,927 filed Nov. 13, 1995, medical probe is provided with a tubular inner bushing 56 made from a stainless steel hypotube or other suitable material. The proximal end of inner bushing 56 is press fit within the distal end of passageway 36 and secured within catheter shaft 32 by any suitable means such as an adhesive (not shown). Intermediate and outer bushings 57 and 58, each made form a stainless steel hypotube or other suitable material, extend concentrically around the distal extremity of inner bushing 56. The proximal extremities of flex strips 47 extend longitudinally along the outside of outer bushing 58. The proximal extremities of support strips 44 extend with an interference fit between bushings 56, 57 and 58 so as to secure arm proximal extremities 38a to catheter shaft 32. More specifically, the proximal ends of the support strips 44 from four of the eight arms 38, such arms 38 circumferentially spaced approximately 90° relative to each other, extend between inner and intermediate bushings 56 and 57. The proximal ends of the support strips 44 from the other four arms 38, such other arms 38 circumferentially spaced approximately 90° relative to each other, extend between intermediate and outer bushings 57 and 58. In this manner, support strips 44 of adjacent arms 38 alternate around the catheter shaft from extending between bushings 56 and 57 and bushings 57 and 58.

Flex strips 47 with traces 49 thereon extend longitudinally in a proximal direction from arm proximal extremities 38a as shown in FIG. 2. Lead or electrical means in the form of eight cables 66 extend through additional lumen 67 of catheter shaft 32. Each cable 66 includes a plurality of at least eight conductive filaments or conductors (not shown). The distal ends of cables 66 are respectively secured to the proximal ends of flex strips 47 and the conductive fibers of the cables are connected to traces 49 on the flex strips 47. An encapsulant made from any suitable material such as epoxy extends through and circumferentially around inner bushing 56 on both sides of the proximal ends of flex strips 47 and the distal ends of cables 66 for providing a flexible body 68 which extends distally of catheter shaft 32 to proximal extremities 38a of arms 38.

Arms 38 extend distally of catheter shaft 32 so that adjacent arms 38 extend at an acute angle relative to each other when basket assembly 37 is in an expanded position as shown in solid lines in FIG. 1. Arm distal extremities 38b are joined together as shown in FIGS. 1 and 3 so that adjacent distal extremities 38b meet at an acute angle relative to each other. As more fully described in U.S. patent application Ser. No. 08/555,927 filed Nov. 13, 1995, tip 71 serves as the means of medical probe 31 for interconnecting the distal extremities 38b of arms 38. A disk 72 formed from first and second plate members 73 and 74 is disposed at a substantially right angle to central longitudinal axis 33 for securing together arm distal extremities 38b. Disk 72 is provided with a plurality of slots (not shown) extending through the top and bottom surfaces 76 and 77 thereof for receiving distal stubs 78 of support strips 44. An enlarged tig weld 81 is provided on the end of each distal stub 78 for retaining the arm distal extremity 38b within the slot of disk 72. Disk 72 is encapsulated within any suitable elastomeric and soft material such as silicone 82 for providing tip 71 with a soft, rounded distal end 83.

Means is included within basket assembly 37 for inhibiting the formation of thrombus thereon when the basket assembly is disposed in the chamber of the heart. In this regard, and as more fully described in U.S. patent application Ser. No. 08/555,927 filed Nov. 31, 1995, webbings (not shown) made from any suitable elastomeric and durable material such as tecoflex polyurethane is provided between the vees formed by adjacent proximal extremities 38a and the vees formed by adjacent distal extremities 38b of arms 38. In addition, the basket assembly 37 is coated with a suitable anti-thrombogenic agent as for example heparin, hirudin and streptokinase containing coatings (not shown) prior to insertion of probe 31 into the body.

A handle means is coupled to proximal extremity 32a of catheter shaft 32 and includes a three-fold fitment 91 secured to the proximal extremity 32a for moving catheter shaft 32 and basket assembly 37 longitudinally through a lumen of a body into the heart (see FIG. 1). Fitment 91 is provided with a central or in line fitting 91a and left and right fittings 91b and 91c disposed on either side of central fitting 91a. Left fitting 91b is in communication with additional lumen 67 so as to permit cables 66 to extend from catheter shaft 32. A connector 92 is attached to the proximal end of cables 66 and is provided with a plurality of pins (not shown) electrically coupled to the conductors of cables 66 for permitting electrical functions to be performed with respect to electrodes 46 carried by basket assembly 37. A conventional flexible strain relief 93 made from any suitable material such as polyolefin is concentrically mounted over the distal end of fitment 91 and the proximal end of catheter shaft 32 for providing a transition in stiffness between the catheter shaft 32 and fitment 91.

The expandable means carried by distal extremity 32b of catheter shaft 32 further includes an additional longitudinally-extending member in the form of a rotatable arm member 96 similar to the rotatable arm member described in copending U.S. patent application Ser. No. 08/718,780 filed Sep. 24, 1996, incorporated herein by this reference (see FIG. 1–4). The rotatable arm member or arm 96 has a proximal extremity 96a slidably disposed within central passageway 36 of catheter shaft 32 and a distal extremity 96b extending beyond the catheter shaft to tip 71. Arm 96 is made from any suitable material such as a superelastic shape memory alloy like Nitinol and is formed with a predetermined bowed shape in its distal extremity 96b. As shown in FIG. 5, the cylindrical arm 96 is circular in cross-section with an outer diameter of approximately 0.016 inch. The distal end of rotatable arm 96 is rotatably coupled to tip 71 to permit arm distal extremity 96b to swing within basket assembly 37 as the arm 96 is rotated at tip 71 about central longitudinal axis 32. Specifically, as shown in FIG. 3, plate members 73 and 74 of disk 72 are provided with a central hole 97 extending between opposite planar surfaces 76 and 77 of the disk. A tig weld 98 is formed on the end of arm 96 distal of disk 72 for precluding the arm 96 from being pulled proximally through hole 97. A clamp 101 is secured about arm 96 proximal of disk 72 for limiting relative longitudinal movement between arm 96 and disk 92 when a compressive force is exerted on the arm 96. A helical spring 102 is wrapped between tig weld 98 and disk 72 and extends distally of disk 72 for further securing silicone 82 to tip 71.

Means is included within medical probe 31 for inhibiting the formation of thrombus where rotatable arm 96 extends from central passageway 36 into basket assembly 37. This means includes right fitting 91c which communicates with passageway 36 and permits a saline or other flushing solution to be introduced through the passageway into basket assembly 37. This flow of saline solution further inhibits the formation of thrombus at the vees between adjacent proximal extremities 38a of basket arms 38.

The handle means coupled to the proximal extremity of catheter shaft 32 further includes a handle 111 of the type described in U.S. Pat. No. 5,478,330, incorporated herein by this reference, for rotating arm 96 about central longitudinal axis 93 within basket assembly 37 and for bowing distal extremity 96b of the rotatable arm 96 radially outwardly from axis 93 into a space 41 between basket arms 38. Handle 111 includes a body 112 having finger actuatable means in the form of tubular sleeve 113 rotatably mounted thereon. Proximal extremity 96a of rotatable arm 96 extends through central fitting 91a of fitment 91 and a second fitting in the form of two-fold or Y-fitment 116 having central and side fittings 116a and 116b. The distal end of handle body 112 is secured to central fitting 116a. Proximal extremity 96a extends from Y-fitment 116 into body 112 where it is coupled to rotatable sleeve 113. Rotation of sleeve 113 in a clockwise direction relative to body 112 causes rotatable arm 116 to move distally within catheter shaft 32. Conversely, rotation of sleeve 113 in a counterclockwise direction causes rotatable arm 96 to move proximally within catheter shaft 32.

At least one additional electrode in the form of ring electrode 121 is included within the expandable means carried by the distal extremity of catheter shaft 32 (see FIGS. 1, 4 and 5). Ring electrode 121 is made from any suitable material such as platinum or a platinum alloy. Means is provided for slidably mounting ring electrode 121 about distal extremity 96a of rotatable arm 96 and includes at least one layer of a suitable insulating material such as low density polyethylene. The flexible sheet of material is formed as an elongate tubular member or tube 122 and is concentrically mounted about rotatable arm 96. Inner plastic tube 122 has an inner diameter which closely approximates the outer diameter of proximal extremity 96a to inhibit buckling of the proximal extremity 96a when a compressive load is exerted on rotatable arm 96. The material of inner tube 122 has a low coefficient of friction to facilitate sliding of the tube 122 on rotatable arm 96. The inner plastic tube 122 extends proximally from a position within basket assembly 37 through central passageway 96 of catheter shaft 32 and out central fitting 91a of fitment 91. The proximal extremity of inner plastic tube 122 is secured to Y-fitment 116. Ring electrode 121 is mounted around the outside of inner plastic tube 122 at a distance of approximately 0.4 inch from the distal end of tube 122 by any suitable means such as an adhesive (not shown).

At least one additional layer of insulating material formed as a tubular member 123 is concentrically mounted about ring electrode 121 and the distal extremity of inner plastic tube 122 as illustrated in FIGS. 1, 4 and 5. Tubular member 123 or outer plastic tube 123 is made from any suitable flexible material such as a low density polyethylene and, together with ring electrode 121 and inner plastic tube 122, form a pliable electrode assembly 126. The distal ends of tubes 123 and 122 are heat sealed together and shrunk closely about rotatable arm 96 to form the distal end 127 of electrode assembly 126. An elongate tubular member or tube 128 made from any suitable material having sufficient torquability and column strength is concentrically mounted about inner plastic tube 122 and rotatable arm 96 within central passageway 36. Suitable materials for torquable tube 128 include metal, plastic or a composite material such as a plastic with metal braids therein. The proximal end of outer plastic tube or balloon 123 is secured to the distal end of torquable tube 128, as shown in FIG. 2, to define the proximal end 129 of electrode assembly 126. The electrode assembly 126 has a length between its proximal and distal ends 129 and 127 of approximately 0.6 inch and ring electrode 121 is disposed approximately midway between ends 129 and 127.

Balloon 123 extends radially outwardly from inner plastic tube 122 to an outer diameter at its farthest point of approximately 0.1 inch to define an annular chamber 131 within electrode assembly 126. Expandable means in the form of any suitable material such as polyurethane foam 132 is disposed in annular chamber 131 for urging balloon 123 radially outwardly from inner plastic tube 122. A plurality of longitudinally spaced-apart ports or holes 133 extend through balloon 123. The array of holes 133 direct any fluids within annular chamber 131 into the tissue.

It should be appreciated that electrode assembly can have other embodiments and be within the scope of the present invention. For example, electrode assembly 126 can be formed with a porous plastic tube 128 made from any suitable material such as pebax. The plastic tube 128 is provided with an array of holes 133 therein.

Torquable tube 128 is spaced radially outwardly from inner plastic tube 122 so as to form an annular passageway 134 between tubes 128 and 122 which communicates with annular chamber 131 (see FIGS. 4–6). The torquable tube 128 extends proximally from central fitting 91a where it is secured at its proximal end to Y-fitment 116. Inner plastic tube likewise extends proximally from central fitting 91a where it is secured at its proximal end within fitment 116. Side fitting 116b in fitment 116 communicates with annular passageway 134 and thus annular chamber 131.

Y-fitment 116 is spaced proximally from fitment 91 so that proximal and distal longitudinal movement of handle 111 relative to fitment 91, as shown by the arrow in FIG. 1, causes distal extremity 96a of the rotatable arm 96 and electrode assembly 126 thereon to bow outwardly from longitudinal axis 33 in basket assembly 37. A reinforcing tube 136 made from stainless steel or any other suitable material extends distally from fitment 91 into central fitting 116a for inhibiting kinking of torquable tube 128 and rotatable arm proximal extremity 96a when a compressive longitudinal force is exerted on handle 111. A conventional flexible strain relief 137 substantially similar to strain relief 93 is concentrically mounted over the distal end of fitment 116 and the proximal end of reinforcing tube 136 for inhibiting bending of tubes 136 and 128 and rotatable arm 96 at the fitment 116.

An additional lead means in the form of electrical wire 141 is coupled at its distal end to ring electrode 121. Wire 141 extends proximally through annular passageway 134 and fitment 116 and through handle body 112 to a cable 142 extending from body 112. Cable 142 has a pin connector 143 on the free end thereof for connection to a controller (not shown) which can include a radio frequency generator. Temperature sensing means in the form of thermocouple wires 144 also extend from connector 143 through passageway 134 to ring electrode 121 of pliable electrode assembly 126 for permitting the temperature of electrode 121 to be monitored outside of the body.

In operation and use, basket assembly 37 can be introduced by means of an introducer catheter (not shown) through a vessel of the body into a chamber of the heart, such as the left ventricle, formed by the heart wall. Once the basket assembly 37 is within the ventricle and tip 71 has engaged the apex of the ventricle, the introducer catheter is retracted relative to medical probe 31 so as to permit arms 38 to bow outwardly and basket assembly 37 to move to its expanded position. The bowing of arms 38 causes electrodes 46 to engage the wall of the heart. Electrical signals from the endocardium are detected by electrode pairs 48 and transmitted via pin connector 92 to the controller (not shown) which generates a map of the endocardium for facilitating location of an arrhythmia. Should it be desirable to ablate the wall of the heart by means of basket assembly 37, radio frequency energy can be supplied by the controller to one or more of electrodes 46 for creating lesions in the heart wall. It should also be appreciated that medical probe 31 can be used solely for detecting electrical signals from the endocardium and be within the scope of the present invention.

Pliable electrode assembly 126 expands under the force of foam 132 when basket assembly 37 moves out of the introducer catheter. Rotatable arm 96 and pliable ablation electrode assembly 126 slidably mounted thereon can be used for detecting electrical signals from the endocardium in the spaces 41 between basket arms 38 for permitting fine mapping and ablation of the heart. In this regard, handle 111 can be rotated relative to catheter shaft 32 and fitment 91 so that the predetermined bow formed in distal extremity 96b is aligned about longitudinal axis 33 with a desired space 41 between the basket arms 38. Electrode assembly 126 can be moved distally on rotatable arm 96 ky rotating sleeve 113 in a counterclockwise direction on handle body 112 and the electrode assembly 126 can be moved proximally on arm 96 by rotating sleeve 113 in a clockwise direction on body 112. Rotatable arm 96 and electrode assembly 126 are bowed outwardly into the desired space 41 so as to engage the wall 148 of the heart, as shown by the phantom lines in FIG. 1, by moving handle 111 distally relative to fitment 91. Torquable tube 128 has a sufficient column strength to permit relative slidable movement between pliable electrode assembly 126 and rotatable arm 96. Proximal movement of the handle 111 relative to fitment 91 causes the arm 96 to collapse toward central longitudinal axis 33 if realignment of arm 96 within basket assembly 37 is desired. Handle 111 and sleeve 113 thereon thus permit angular, longitudinal and radial movement of electrode assembly 126 relative to basket assembly 37.

Once electrode assembly 126 and holes 133 have been placed in a desired position on the endocardium, a conductive liquid such as a saline solution can be introduced through side fitting 116b to electrode assembly 126 and cause the saline solution to ooze outwardly through the holes 133. The electrical signals from the endocardium are transmitted by means of the conductive liquid to ring electrode 121. Alternatively, electrode assembly 126 and ring electrode 121 can be pressed against the endocardium by means of rotatable arm 96 to detect signals through the holes 133 provided in porous balloon 123. The operating physician can thus use electrode assembly 126 to locate the site of the arrhythmia for ablation. The electrode assembly 126 can be moved both longitudinally and radially within space 41 by the rotatable arm 96 in this regard.

Pliable electrode assembly 126 can also be used to form lesions on selected portions of the heart wall, for example, between arms 38 of basket assembly 37. As more specifically described in copending U.S. patent application Ser. No.

08/611,656 filed Mar. 6, 1996, radio frequency energy is applied to ring electrode 121 and emitted into annular chamber 131. The saline solution creates a conductive path for passage of radio frequency energy from ring electrode 121 to the wall of the heart. The spacing between holes 133 and the size of the holes 133 can be adjusted to tailor the lesion so created.

The irregularities in the topology of the heart wall can be accommodated by pliable ablation electrode assembly 126. Specifically, flexible balloon 123 can bend to conform with the shape of the endocardium to thus ensure good contact between the electrode assembly and the heart wall. The flow of saline solution from holes 133 further serves to inhibit the formation of coagulum on pliable electrode assembly 126.

Movable electrode assembly 126 can take the place of several fixed electrodes provided on arm 96 for ablation purposes. Thus, the number of electrodes required on rotatable arm 96 for ablation is reduced and the number of wires extending through catheter shaft 32 to handle 111 is also reduced. Since a conventional ablation electrode includes multiple wires, for example a wire for providing radio frequency energy to the electrode and at least one wire for monitoring the temperature of the electrode, the number of eliminated wires can be significant.

The integration of the movable ablation electrode into probe 31 is advantageous in several respects. The need for two catheters to accomplish a mapping and ablation procedure in the heart chamber is eliminated. In addition, the slidable mounting of electrode assembly 126 on a rotatable arm 96 coupled to the proximal and distal ends of basket assembly 37 provides significant support and stability to the electrode assembly 126. The assembly 126 is thus less likely to flop out of position when placed against the heart wall. The probability of the ablation electrode entangling with arms 38 of basket assembly 37 is also minimized.

An electrode of the type described above can be slidably mounted on other elongate members of a basket assembly and be within the scope of the present invention. For example, the electrode can be slidably mounted on one of mapping arms 38 of basket assembly 37. As another example, the electrode can be slidably mounted on a mapping or support arm of a sector basket of the type described in International Patent Application No. PCT/US96/18204 filed Nov. 13, 1996.

Rotatable arm 96 has been described as having a distal extremity which is cylindrical in shape. However, it should be appreciated that the distal extremity of rotatable arm 96 can have other conformations and be within the scope of the present invention. For example, as shown in FIG. 7, rotatable arm 96 can have a distal extremity 146 which is rectangular in cross-section. More specifically, distal extremity 146 can be formed of opposite first and second planar surfaces 147 and thus be generally strip-like. The flattened distal extremity 146 can be created by swaging the otherwise circular in cross-section rotatable arm 96 at its distal extremity. In operation, distal extremity 146 is encouraged by its rectangular shape to bend in a predetermined manner so that one of planar surfaces 147 faces the endocardium. Sideways bending of distal extremity 146 is inhibited so that additional stability is provided to electrode assembly 126 carried by the rotatable arm. The circular cross-section of arm proximal extremity 96a provides the desired torsional rigidity to the rotatable arm 96 for effectively rotating distal extremity 146 within basket assembly 37.

Figure 8:
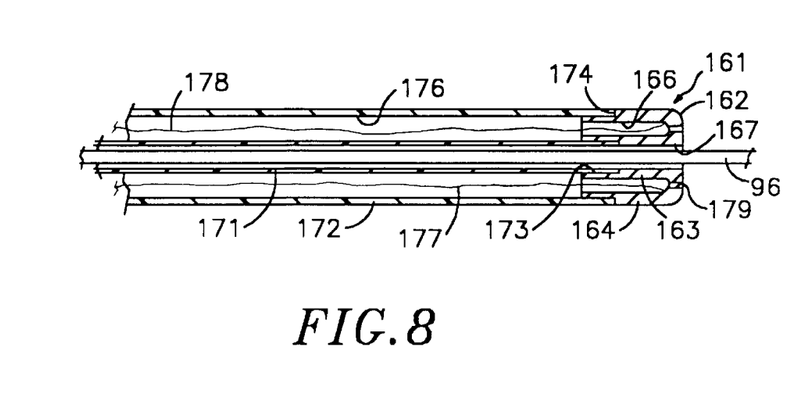
FIG. 8 is a cross-sectional view, similar to FIG. 4, of another embodiment of the movable electrode of the catheter of FIG. 1.

Other embodiments of the slidable electrode of the present invention can be provided. As shown in FIG. 8, an electrode in the form of tip electrode 161 is slidably carried by distal extremity 96b of rotatable arm 96. Like reference numerals have been used to describe like elements in FIGS. 1–7 and in FIG. 8. Tip electrode 161 is made from any suitable material such as platinum or a platinum alloy and is provided with a rounded distal end 162 and inner and outer tubular walls for forming an annular chamber 166 in the electrode 161. A bore 167 extends longitudinally through inner tubular wall 163 and rounded end 162 for slidably receiving rotatable arm 96.

First and second sheets of flexible material in the form of inner and outer tubular members or tubes 171 and 172 are secured to the proximal extremity of electrode 161. Inner tube 171 is made from any suitable material such as Teflon so as to have a low coefficient of friction for permitting tube 171 to easily slide on rotatable arm 96. Outer tube 172 is made from any suitable material such as nylon or polyurethane and has a sufficient column strength to move electrode 161 along rotatable arm 96. Inner tubular wall 163 is provided with an annular recess 173 into which the distal end of inner plastic tube 171 can be secured by any suitable means such as heat shrinking tube 171 about barbs (not shown) formed on electrode 161 in recess 173. Outer tubular wall 164 is provided with an annular recess 174 into which the distal end of outer plastic tube 172 is secured by any suitable means such as an adhesive (not shown). Inner plastic tube 171 extends proximally from electrode 161 through catheter shaft 32 and is secured at its proximal end to Y-fitment 116. Outer plastic tube 172 extends to the distal end of torquable tube 128.

Tubes 172 and 128 are spaced radially outwardly from inner plastic tube 171 to provide an annular passageway 176 which extends the length of catheter shaft 32 and communicates with electrode chamber 166. Lead means in the form of an electrical wire 177 is electrically coupled at its distal end to tip electrode 161 and extends through passageway 176 and handle body 112 to cable 142 and connector 143. Wire 177 thus permits electrical functions to be performed by tip electrode 161, such as detecting signals from the epdocardium or creating lesions in the wall of the heart. Thermocouple wires 178 also extend through annular passageway 176 and are secured at their distal ends to the inside of tip electrode 161 for measuring the temperature of the electrode.

Annular passageway 176 can also serve as means for supplying a cooling liquid to tip electrode 161 so as to permit deeper lesions to be created in the wall of the heart as more specifically set forth in copending U.S. patent application Ser. No. 08/381,198 filed Jan. 31, 1995 (Our file A-56272-4). Briefly, a cooling liquid such as a saline solution can be introduced into passageway 176 and thus internal electrode chamber 166 by means of side fitting 116b. A plurality of circumferentially spaced-apart ports or holes 179 extend from internal chamber 166 through rounded end 162 for permitting the cooling solution to exit the internal chamber.

In operation and use, tip electrode 161 can be longitudinally positioned on rotatable arm 96 and angularly positioned in a space 41 between basket arms 38 to detect electrical signals from the endocardium. Alternatively, electrical energy supplied by a radio frequency generator coupled to connector 143 can be supplied to tip electrode 161 for creating lesions in the heart wall.

Figure 9:
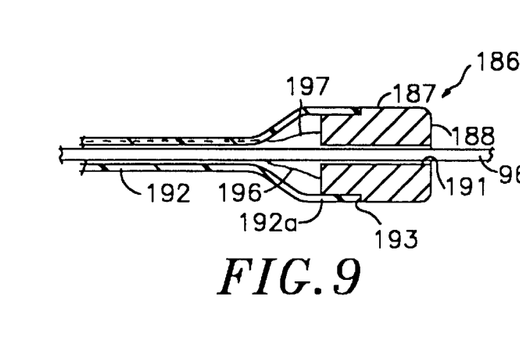
FIG. 9 is a cross-sectional view, similar to FIG. 4, of a further embodiment of the movable electrode of the catheter of FIG. 1.

A further embodiment of a tip electrode for use with rotatable arm 96 is shown in FIG. 9. Cylindrical tip electrode 186 shown therein is made from platinum or a platinum alloy or any other suitable material and has an outer surface 187 which is circular in cross-section and a rounded distal end 188. A longitudinally-extending bore 191 extends through electrode 186 for slidably receiving rotatable arm 96. A tubular member or tube 192 made from any suitable material such as nylon or polyurethane is concentrically mounted about rotatable arm 96 along the length thereof. Plastic tube 192 has a distal extremity 192*a* which seats within an annular recess 193 provided in outer surface 187 at the proximal end thereof. Distal extremity 192*a* is secured within recess 193 by any suitable means such as an adhesive (not shown). Tube 192 necks down from electrode 186 to an inner diameter which closely approximates the outer diameter of rotatable arm 96 and extends through central passageway 36 of catheter shaft 32. The proximal extremity (not shown) of plastic tube 192 is secured to fitment 116.

Lead means in the form of electrical wire 196 has a distal end electrically coupled to tip electrode 186. Wire 196 extends through plastic tube 192 and handle 111 to cable 142 and connector 143 for permitting electrical signals detected by electrode 186 to be accessed at connector 143 or, alternatively, to permit radio frequency energy to be supplied to the tip electrode 186. Thermocouple wires 197 also extend through plastic tube 192 and are secured to tip electrode 186 for monitoring the temperature of the electrode.

The operation and use of tip electrode 186 is substantially similar to the operation and use of tip electrode 161 described above. Briefly, electrode 186 can be slid proximally and distally along rotatable arm 96 by means of rotatable sleeve 113 on handle 111 for positioning the electrode longitudinally within basket assembly 37. Rotation of handle 111 serves to rotate arm 96 about longitudinal axis 33 and thus angularly position electrode 161 within basket assembly 37. Tip electrode 161 can be placed against the endocardium in a space 41 between basket arms 38 by distal movement of handle 111 relative to fitment 91. Tube 192 inhibits buckling of the proximal extremity 96*a* of rotatable arm 96 during such bowing of arm distal extremity 96*b*. Mapping and/or ablation can be performed by the tip electrode 186.

Figure 10:
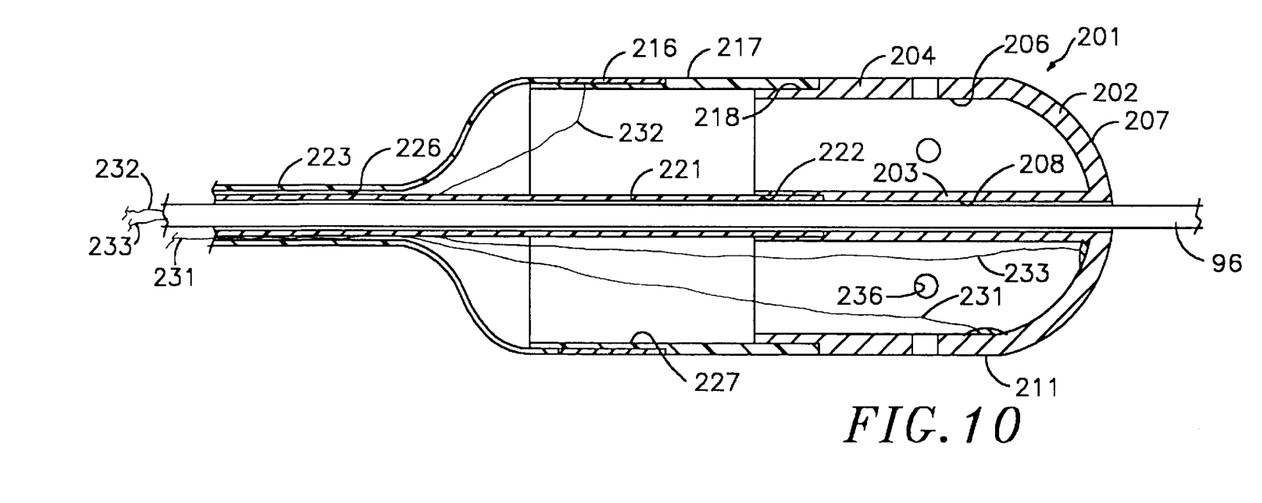
FIG. 10 is a cross-sectional view, similar to FIG. 4, of another embodiment of the movable electrode of the catheter of FIG. 1.

In a further embodiment of the present invention, an electrode assembly 201 having a tip electrode 202 for use with medical probe 31 is illustrated in FIG. 10. Tip electrode 202 has aspects similar to both electrodes 161 and 186 described above. The tip electrode 202 is made from platinum or a platinum alloy or any other suitable material and has inner and outer tubular walls 203 and 204 for forming an annular internal chamber 206 terminating at rounded distal end 207 of the tip electrode. A central bore 208 extends longitudinally through inner tubular wall 203 and exits the distal end 207 for slidably receiving rotatable arm distal extremity 96*b*. The rotatable arm 96 is included within the means for moving large electrode 202 between a position close to longitudinal axis 33 into a space 41 between basket arms 38 for engaging the wall of the heart.

It is desirable to use an ablation tip electrode whose size has demonstrated the ability to create significantly large lesions in the tissue of the heart wall using typical radio frequency power levels. Tip electrode 202 is relatively large in size and has an external diameter ranging from three to nine French, preferably greater than five French such as ranging from five to eight French and more preferably ranging from six to seven French. As such, the external diameter of the tip electrode 202 is preferably larger than the internal diameter of central passageway 36 of catheter shaft 32 so that tip electrode 202 cannot be withdrawn from the catheter shaft and is thus permanently disposed within basket assembly 37. The tip electrode 202 has a length ranging from three to eight millimeters and preferably approximately four millimeters. Outer wall 204 and rounded end 207 form an outer surface 211 for tip electrode 202 which has an area ranging from approximately 10 to 40 mm$^2$.

Electrode assembly 201 further includes a ring electrode 216 located proximal of tip electrode 202. Ring electrode 216 has an outer diameter equal to the outer diameter of tip electrode 202 and a longitudinal dimension or length of approximately one millimeter. The ring and tip electrodes 216 and 202 are interconnected by means of a tube member 217 made from any suitable material such as nylon, polyurethane or polyolefin having a distal end secured within an annular recess 218 formed in the proximal end of tip electrode 202. Ring electrode 216 is concentrically mounted about the proximal extremity of tube member 217.

Electrode assembly 201 has an inner tubular member or plastic tube 221 made from any suitable material such as polyethylene concentrically mounted about distal extremity 96*b* of rotatable arm 96. The distal end of inner plastic tube 221 is secured within an annular recess 222 provided on the inside of tubular wall 203. The proximal extremity (not shown) of the inner plastic tube 221 is secured to Y-fitment 116. Rounded distal end 207, forming bore 208, and inner plastic tube 221 are included within the means for slidably mounting electrode assembly 201 on rotatable arm 96. An outer plastic tube 223 made from any suitable material such as nylon, polyurethane or polyolefin abuts the proximal end of ring electrode 216 and is secured around the outside of the proximal end of tube member 217. Outer plastic tube 223 necks down to an external diameter of approximately three French and to an internal diameter larger than the outer diameter of plastic tube 221. The proximal end of outer plastic tube 223 is secured to torquable tube 128 (not shown) in the same manner as balloon 123 discussed above is secured to the torquable tube 128. As can be seen, the catheter shaft, that is tubes 128 and 223, preferably has an external diameter that is 30% to 50% smaller than the external diameter of tip electrode 202.

The annular space provided between outer and inner plastic tubes 223 and 221 serves as a lumen 226 which communicates with annular chamber 206 and the annular space 227 between tube member 217 and inner plastic tube 221. First and second lead means in the form of electrical wires 228 and 229 extend through lumen 226 and are connected respectively to tip and ring electrodes 202 and 216 by any suitable means such as solder. The proximal ends (not shown) of wires 231 and 232 extend through handle 111 and cable 142 and are electrically coupled to connector 143. Thermocouple wires 233 extend from connector 143 through lumen 226 to tip electrode 202 permitting the temperature of the tip electrode to be monitored outside of the body. Wires 233 are connected to electrode 202 by solder or any other suitable means.

Means for cooling electrode assembly 201 is included within medical probe 31 and includes side fitting 116*b* which communicates with annular lumen 226. A suitable cooling liquid such as a saline solution can be introduced into annular chamber 206 of the tip electrode 202 for permitting deep lesions to be created in the wall of the heart when radio frequency energy is supplied to the tip electrode 202. A plurality of circumferentially spaced-apart ports or holes 236 are provided in outer tubular wall 204 for permitting the saline solution to flow from annular chamber 206 into the heart.

In operation and use, medical probe 31 with electrode assembly 201 is introduced into a chamber of the heart by means of an introducer catheter in the manner discussed above. Basket arms 38 collapse around electrode assembly 201 when the distal end of medical probe 31 is disposed within the introducer catheter. Once basket assembly 37 has been deployed into the heart and suitable mapping of the endocardium has been performed by electrode pairs 48 on the basket assembly 37, the electrode assembly 201 can be longitudinally positioned on rotatable arm 96 and then positioned in a space 41 between basket arms 38 by rotation of arm 96 relative to the basket assembly 37. When distal extremity 96a of rotatable arm 96 is bowed outwardly relative to longitudinal axis 33, electrode assembly 201 coaxially mounted thereon can engage the endocardium. Tip electrode 202 and ring electrode 216 serve as an electrode pair for permitting a bipolar signal to be transmitted out of the body for further mapping of the heart wall. The operating physician can further use this information to confirm that electrode assembly 201 has been desirably positioned on the endocardium for performing an ablation procedure.

Ring electrode 216 can also be utilized as an ablation electrode for creating lesions in the heart wall. It should be appreciated that a plurality in excess of two longitudinally spaced-apart electrodes can be provided on electrode assembly 201 for creating linear lesions and be within the scope of the present invention.

As discussed above, coolant means can be provided in annular chamber 206 for permitting deep lesions to be formed in the myocardium by tip electrode 202. As an alternative to perfusing the coolant into the blood stream, as disclosed above, a coolant return lumen can be provided in catheter shaft 32 and be within the scope of the present invention. It should be appreciated, that a tip electrode 202 without cooling means can be provided and be within the scope of the present invention.

Figures 11, 17:
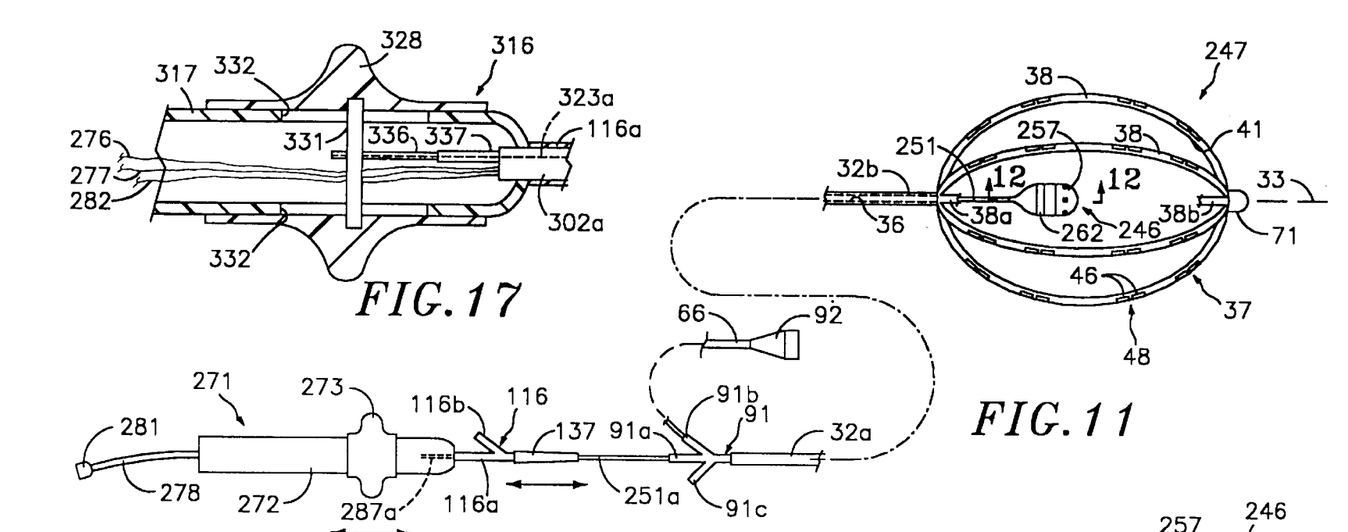
FIG. 11 is a side elevational view, partially cut away, of another embodiment of the endocardial mapping catheter with movable electrode of the present invention.
FIG. 17 is a cross-sectional view of a portion of the handle means of the endocardial mapping catheter of FIG. 14.
Figures 12, 13:
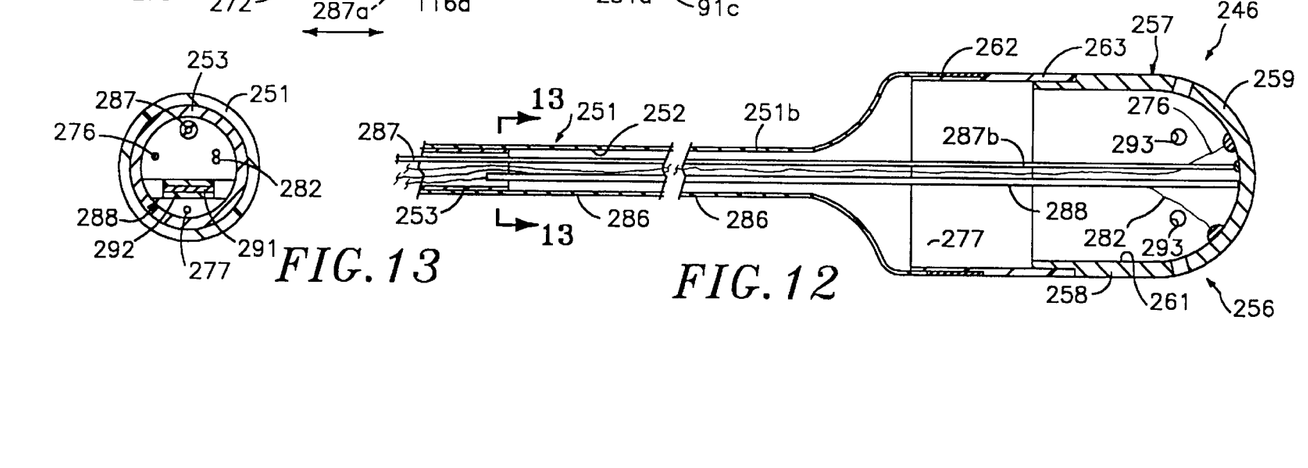
FIG. 12 is a cross-sectional view of the movable electrode of the catheter of FIG. 11 taken along the line 12—12 of FIG. 11.
FIG. 13 is a cross-sectional view of the movable electrode of the catheter of FIG. 11 taken along the line 13—13 of FIG. 12.

A large ablation electrode for use in a basket-like assembly can be decoupled from an elongate member such as ablation arm 96 and be within the scope of the present invention. FIGS. 11–13 illustrate an ablation catheter 246 which is integrally coupled with a medical probe 247 substantially similar to medical probe 31 described above. Like reference numerals have been used to show like components shown in FIGS. 11–13 and in FIGS. 1–6 and 10. Unlike medical probe 31, medical probe 247 does not includes a rotatable arm 96 slidably disposed in central passageway 36 of catheter shaft 32 and rotatably coupled at its distal end to tip 71 of basket assembly 37. Instead, ablation catheter 246 is slidably disposed in the central passageway 36.

Ablation catheter 246 includes a flexible elongate tubular member in the form of catheter shaft 251 made from any suitable material such as nylon, polyurethane or polyolefin and having an external size ranging from two to six French and preferably ranging from three to four French. Catheter shaft 251 has proximal and distal extremities 251a and 251b and a length so that when the distal extremity 251b is in a chamber of the heart the proximal extremity 251a is outside of the body. A central lumen or passageway 252 extends in catheter shaft 251 between its extremities 251a and 251b (see FIG. 12). An additional flexible elongate tubular member in the form of reinforcing tube 253 extends through central passageway 252 along the length of catheter shaft 251. Reinforcing tube 253 provides torsional rigidity and a degree of stiffness for pushability to the portion of catheter shaft 251 through which it extends. Catheter shaft 251 is heat shrunk or otherwise suitably secured to reinforcing tube 253. Catheter shaft 251 can alternatively be made from a composite material incorporating metallic braid or coil structures thereby eliminating the need for reinforcing tube 253.

An electrode assembly 256 adapted to engage the wall of the heart and substantially similar to electrode assembly 201 is carried by distal extremity 251b of the catheter shaft. Electrode assembly 256 is permanently disposed within basket assembly 37 and includes at least one electrode in the form of a tip electrode 257 having a size and surface area similar to tip electrode 202 described above. Electrode 257 thus has a diameter larger than the external diameter of catheter shaft 251 and the internal diameter of central passageway 36. Tip electrode 257 is made from any suitable conductive material such as platinum or a platinum alloy and is formed from an outer tubular wall 258 and a rounded distal end 259. Electrode assembly 256 further includes a ring electrode 262 substantially similar to ring electrode 216. Ring electrode 262 is secured to tip electrode 257 by means of a tube member 263 substantially similar to tube member 217. Catheter shaft 251 expands radially outwardly to secure to tube member 263 in the same manner as discussed above with respect to electrode assembly 201. The catheter shaft 251 is included within the means of ablation catheter 246 for moving electrode assembly 256 mounted thereon from a position close to longitudinal axis 33 into a space 41 between basket arms 38.

Handle means is coupled to shaft proximal extremity 32a of medical probe 247 for sliding catheter shaft 251 longitudinally within central passageway 36. The handle means includes a handle 271 of the type described in U.S. Pat. No. 5,478,330 and includes a body 272 having finger actuatable means or circular knob 273 slidably mounted thereon. Proximal extremity 251a of ablation catheter shaft 251 extends proximally through central fitting 91a and is connected to the distal end of Y-fitment 116, which in turn is secured to the distal end of handle body 272.

Lead means is carried by catheter 251 for performing electrical functions with respect to tip and ring electrodes 257 and 262. In this regard, first and second wires 276 and 277 are electrically coupled at their respective distal ends to tip and ring electrodes 257 and 262. Wires 276 and 277 extend proximally from electrode assembly 256 through central passageway 252 and handle body 272 to a cable 278 and pin connector 281 substantially similar to cable and connector 142 and 143 described above. Thermocouple wires 282 are electrically coupled at their distal ends to tip electrode 257 and likewise extend through catheter shaft 251 and handle 271 to connector 281 for permitting the temperature of the tip electrode 257 to be monitored outside of the body.

Means is carried by handle 271 for bending or deflecting catheter shaft 251 at a flexible portion 286 consisting of the portion of catheter shaft 251 extending distally of reinforcing tube 253. An insulated pull element or wire 287 having proximal and distal extremities 287a and 287b is slidably carried in an off-center position in central passageway 252. Distal extremity 287b is secured to the inside of tip electrode 257. Proximal extremity 287a is secured to knob 273 on handle 271. Movement of knob 273 in a proximal direction relative to handle body 272 exerts a tensile force on pull wire 287 and thus causes flexible portion 286 and electrode assembly 256 carried. thereby to bend toward arms 38 of basket assembly 37.

Spring means in the form of a flexible ribbon 288 is included within ablation catheter 246 for returning flexible portion 286 and electrode assembly 255 to their straightened or home position after knob 273 is released by the operating physician. As shown in FIGS. 12 and 13, ribbon 288 includes a strip member 291 made from any suitable material such as stainless steel or Nitinol. A coating 292 of any suitable insulating material encapsulates strip member 291. Ribbon 288 has a tapered proximal end which is staked within the distal end of reinforcing tube 253. The width of ribbon 288 is greater than the inner diameter of reinforcing tube 253 so as to preclude the ribbon from sliding down tube 253. The distal end of the ribbon abuts the inside of ring electrode 262. Ribbon 288 is thus trapped longitudinally between tube 253 and electrode 262. The ribbon 288 has a predetermined straightened shape which urges ablation catheter 246 back to its straightened position once the bending force has bean released from pull wire 287.

Central passageway 252 of ablation catheter 246 communicates with side fitting 116b to permit a saline or other cooling solution to be introduced into internal chamber 261 of tip electrode 257. The saline solution flows from internal chamber 261 through a plurality of circumferentially spaced-apart ports or holes 293 provided in outer tubular wall 258 of the tip electrode.

In operation and use, electrode assembly 256 can be utilized in approximately the same manner as electrode assembly 201 to further map the heart wall and to create a relatively large lesion in the myocardium. Handle 271 and pull wire 287 carried thereby permit tip electrode 257 to be bent off axis, for example in an upward direction in FIG. 12. The tip electrode 257 can thus be selectively steered within basket assembly 37 so as to be placed within a space 41 between basket arm, 38. The temperature of tip electrode 257 can be monitored during the ablation procedure by means of thermocouple wires 282 and the tip electrode 257 can be cooled, if necessary, by a saline solution supplied to internal chamber 261 of the tip electrode by means of side fitting 116b.

The ablation catheter for use with medical probe 247 can have other embodiments and be within the scope of the invention. In FIGS. 14–17, an ablation catheter 301 is provided that can be bent off axis in first and second opposite directions. Like reference numerals are used in FIGS. 14–17 to describe like components shown therein and in FIGS. 10–13. Ablation catheter 301 includes a flexible elongate tubular member in the form of catheter shaft 302 having proximal and distal extremities 302a and 302b. Catheter shaft 302 extends along a longitudinal axis 303 and is made from any suitable material such as plastic. A plurality of lumens in the form of central lumen 304 and at least three circumferentially spaced-apart additional lumens 306, 307 and 308 extend between proximal and distal extremities 302a and 302b of the catheter shaft.

Figure 14:
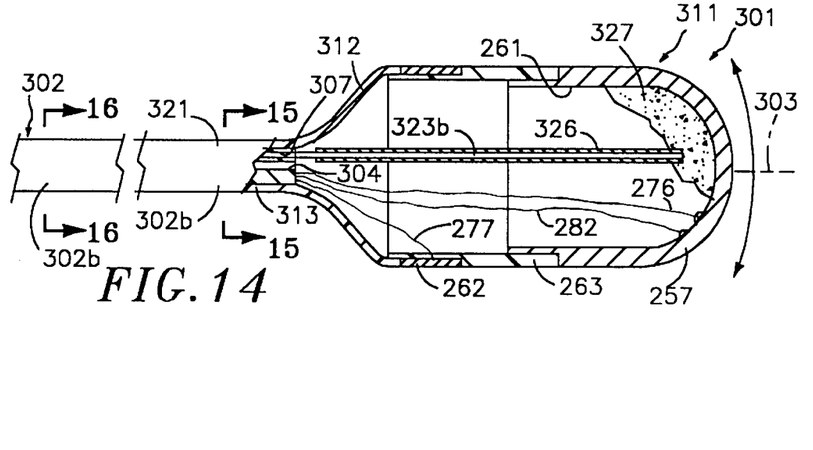
FIG. 14 is a cross-sectional view, similar to FIG. 12, of another embodiment of the endocardial mapping catheter with movable electrode of the present invention.
Figure 15:
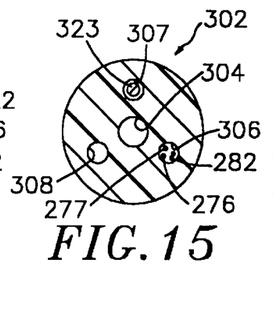
FIG. 15 is a cross-sectional view of the endocardial mapping catheter of FIG. 14 taken along the line 15—15 of FIG. 14.
Figure 16:
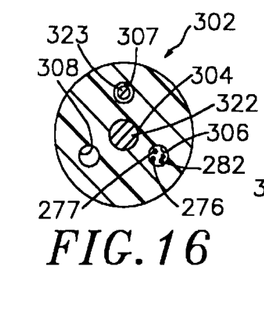
FIG. 16 is a cross-sectional view of the endocardial mapping catheter of FIG. 14 taken along the line 16—16 of FIG. 14.

An electrode assembly 311 is carried by distal extremity 302b of catheter shaft 302. Electrode assembly 311 is substantially similar to electrode assembly 256 and includes tip electrode 257, ring electrode 262 and interconnecting tube member 263. Tip electrode 257 has an outer diameter greater than the outer diameter of catheter shaft 302 and the inner diameter of central passageway 36 in which the catheter shaft 302 is disposed. An additional tubular member in the form of tubular joining member 312 serves as means for connecting electrode assembly 311 to shaft distal extremity 302b. Joining member 312 is made from any suitable polymeric material. It has a distal end secured by any suitable means such as an adhesive (not shown) to the proximal end of tube member 263. Joining member 312 necks down and has a proximal end secured by any suitable means such as an adhesive (not shown) within an annular recess 313 provided in shaft distal extremity 302b. First and second wires 276 and 277 and thermocouple wires 282 extend from electrode assembly 311 through first additional lumen 306 in catheter shaft 302.

The handle means coupled to proximal extremity 302a of catheter shaft 302 includes a handle 316 substantially similar to handle 271 described above. Handle 316 has a handle body 317 substantially similar to handle body 272. Fitment 116 is secured to the distal end of handle body 317. Proximal extremity 302a of catheter shaft 302 extends through central fitting 116a of fitment 116 into the distal end of handle body 317 (see FIG. 17). Wires 276 and 277 and thermocouple wires 282 exit lumen 306 and extend through handle body 317 to cable 278 and connector 281 extending from the proximal end of handle body 317.

Distal extremity 302b of catheter shaft 302 includes a flexible portion 321 for facilitating bending of the distal end of catheter shaft 302. In this regard, a stiffening member in the form of a central core wire 322 made from any suitable material such as stainless steel extends through central lumen 304 from proximal extremity 302a of the catheter shaft 302 to flexible portion 321 (see FIG. 16). The core wire 322 does not extend through flexible portion 321 (see FIG. 15).

Push/pull means is carried by handle 316 for bending catheter shaft 302 at flexible portion 321 in first and second opposite directions as shown by the arrow in FIG. 14. Push/pull means includes a push/pull wire 323 disposed in second additional lumen 307 of catheter shaft 302. Push/pull element or wire 323 has proximal and distal extremities 323a and 323b and is made from any suitable material such as stainless steel. A coating made from any suitable material such as Teflon (not shown) is provided on the outside of wire 323 for facilitating slidable movement of the wire within lumen 307. Wire 323 is circular in cross-section and has a diameter ranging from approximately 0.010 to 0.012 inch so as to be sufficiently flexible to bend with catheter shaft 302. Second additional lumen 307 is circular in cross-section and has an internal diameter ranging from approximately 0.014 to 0.016 inch so as to be only slightly larger in diameter than the outer diameter of wire 323. The aforementioned sizing of wire 323 and the relatively close spacing between the wire 323 and the inside of lumen 307 serves to inhibit buckling of wire 323 in catheter shaft 302 when a compressive force is exerted on the wire 323.

A tubular member in the form of a sleeve 326 made from any suitable material such as stainless steel is disposed within internal chamber 261 of electrode assembly 311 for receiving the distal end of wire 323. Reinforcing sleeve 326 is made from any suitable material such as stainless steel and is crimped or otherwise suitably secured to the distal end of wire 323. The distal end of sleeve 326 is secured to the inside of tip electrode 257 by epoxy 327 or any other suitable means. The proximal end of sleeve 326 is spaced relatively close to the distal end of catheter shaft 302.

Handle 316 includes finger actuatable means in the form of a knob 328 substantially similar to knob 273 for pulling and pushing on wire 323 (see FIG. 17). Knob 328 is slidably mounted on body 317. A rigid transversely-extending pin 331 extends across the inside of tubular knob 328 and is slidably disposed within a pair of opposed slots 332 provided in handle body 317 for limiting the forward and rearward movement of knob 328 on body 317. Proximal extremity 323a of wire 323 extends from catheter shaft 302 into body 317 where it is secured to pin 331. First and second telescoping tubes 336 and 337 each made from stainless steel or any other suitable material are concentrically disposed about wire proximal extremity 323a in handle body 317. Tubes 336 and 337 are each circular in cross-section. First tube 336 has an external diameter of approximately 0.018 inch and is crimped about wire 323. The proximal end of tube 336 is secured within a diametrically-extending bore (not shown) provided in pin 331. Second tube 337 has a distal end secured to proximal extremity 302a of catheter shaft 302 by any suitable means such as an adhesive and a proximal end slidably mounted about first tube 336. Tube 337 has an internal diameter of approximately 0.022 inch and an external diameter of approximately 0.028 inch. Thus, tube 337 has an internal diameter which closely approximates the external diameter of tube 336 to inhibit buckling of the wire when a compressive load is exerted on the wire 323 and tube 336 assembly by knob 328.

Third additional lumen 308 in catheter shaft 302 communicates at its distal end with internal chamber 261 provided in the electrode assembly 311 and at its proximal end with side fitting 116b of fitment 116. A suitable saline or other cooling solution can thus be introduced through lumen 308 into chamber 261 for cooling tip electrode 257 when radio frequency energy is being supplied to the electrode 257 for creating lesions in the wall of the heart. Holes 293 provided in the tip electrode 257 drain the saline solution from electrode assembly 311.

The operation and use of ablation catheter 301 is substantially similar to the operation and use of ablation catheter 246 described above. Push/pull wire 323 permits electrode assembly 311 to be directed off axis 303 in opposite directions within basket assembly 37. For bending flexible portion 321 of catheter shaft 302 in a first direction sideways of longitudinal axis 303, that is in an upward direction in FIG. 14, knob 328 is pulled relative to body 317 to cause wire 323 to move proximally within second additional lumen 307. The proximal end of reinforcing sleeve 326 is spaced a sufficient distance from the distal end of catheter shaft 302 to permit the slight relative longitudinal movement between sleeve 326 and shaft 302. In this manner, flexible portion 321 can be bent to an angle ranging from 0° to 270° relative to longitudinal axis 303 of ablation catheter 301.

For returning flexible portion 321 to its relatively straight or home position by moving flexible portion 321 sideways of longitudinal axis 303 in a second direction opposite of the first direction, knob 328 is pushed forwardly relative to body 317 to cause wire 323 to move distally within catheter shaft 302. The relatively close spacing between the outer cylindrical surface of wire 323 and the internal surface of shaft 302 forming lumen 307 and the concentric support of the proximal and distal ends of wire 323 provided by sleeve 326 and tubes 336 and 337, respectively, inhibit buckling of the wire 323 during straightening of flexible portion 321. Catheter shaft 302, sleeve 326 and tubes 336 and 337 thus serve as support means extending the length of push/pull wire 323 for precluding the wire 323 from buckling when a compressive load is exerted thereon.

Knob 328 can be pushed farther distally on handle body 317 to cause flexible portion 321 to bend beyond its home position in a second direction substantially in the same plane as the first direction. More specifically, distal movement of knob 328 and the subsequent distal longitudinal movement of wire 323 within catheter shaft 302 causes flexible portion 321 to bend in a downward direction in FIG. 14. The concentric support of push/pull wire 323 along substantially its entire length inhibits buckling of the wire 323 and allows flexible portion 321 to bend in the second direction.

Although push/pull wire 323 has been described and shown in connection with ablation catheter 301, it should be appreciated that a concentrically supported push/pull wire for permitting bending of a catheter shaft in opposite first and second directions can be provided in other catheters and be within the scope of the present invention.

The movable or slidable electrodes of the present invention can be utilized with other than full chamber mapping basket assemblies having symmetrically spaced-apart arms. For example, a slidable electrode can be used with a sector-shaped basket having asymmetrically spaced-apart arms such as an endocardial mapping catheter or medical probe 351 of the type described in International Patent Application No. PCT/US96/18204 filed Nov. 13, 1996, incorporated herein by this reference. Medical probe 351, shown in FIGS. 18 and 19, has a flexible elongate tubular member or catheter shaft 352 made from any suitable material such as plastic. Catheter shaft 352 has proximal and distal extremities 352a and 352b and extends along a central longitudinal axis 353. The shaft 352 has an external diameter of approximately nine French. At least one lumen or passageway 354 extends between proximal and distal extremities 352a and 352b parallel to axis 353.

Figures 18, 19:
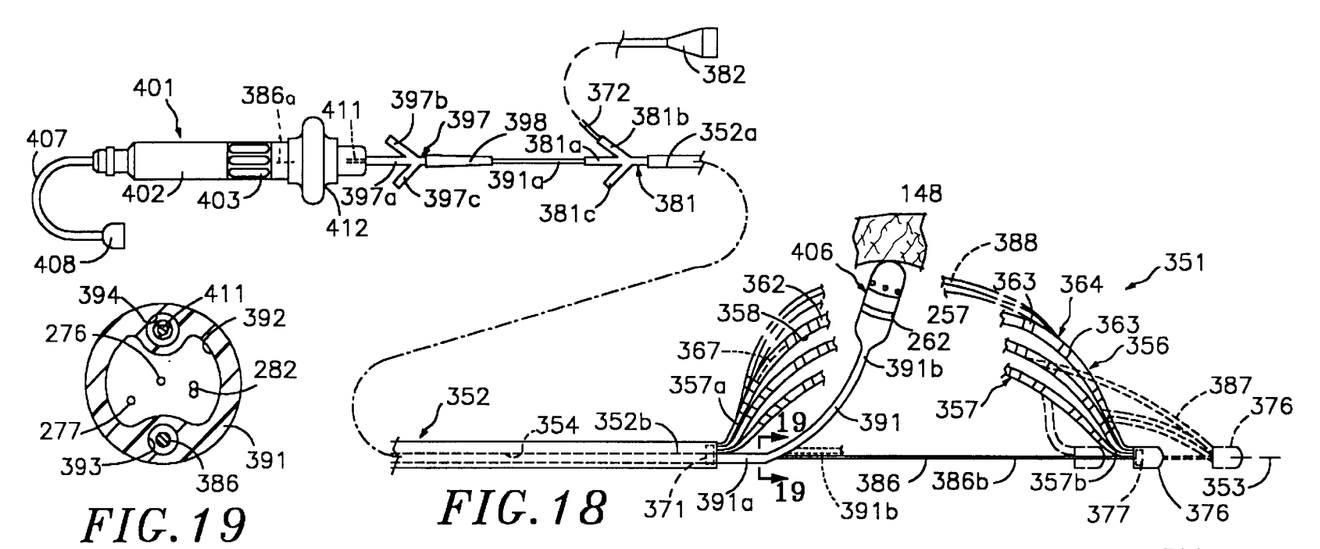
FIG. 18 is a side elevational view of a further embodiment of the endocardial mapping catheter with movable electrode of the present invention.
FIG. 19 is a cross-sectional view of the movable electrode of the catheter of FIG. 18 taken along the line 19—19 of FIG. 18.

An expandable means in the form of a basket-like assembly or sector-shaped basket 356 is carried by distal extremity 352b. Sector-shaped or sector basket 356 is formed from five longitudinally extending spaced-apart members or arms 357 having proximal and distal extremities 357a and 357b. Arms 357 are movable between a first or contracted position in which the arms collapse and extend generally along longitudinal axis 353 and a second or expanded position in which the arms bow outwardly along one side of longitudinal axis 353. Arms 357, which are shown in several expanded positions in FIG. 18, are asymmetrically spaced relatively close together along longitudinal axis 353 in a group. The arms 357 are asymmetrically spaced about axis 353 and subtend an angle ranging from approximately 60° to 180° about the axis and, more specifically, an angle of approximately 120° about the axis. As such, adjacent arms 357 are angularly spaced apart by an angle of approximately 30°. Spaces 358 are provided between adjacent arms 357.

Each of arms 357 is generally strip-like in conformation and has opposite outer and inner planar surfaces 362. Arms 357 each have a predetermined bowed shape, as shown by the solid lines in FIG. 18, provided by a spring-like support member or strip (not shown) extending longitudinally therethrough and preferably made from a superelastic shape memory alloy such as Nitinol. A plurality of electrodes 363 are carried by sector basket or basket-like assembly 356 in longitudinally and radially spaced-apart positions on the basket. More specifically, eight to ten electrodes 363 are carried by each arm 357 and the electrodes 363 on each arm are grouped in four to five pairs so as to provide a plurality of four to five longitudinally spaced-apart electrode pairs 364 on each of the arms. The basket arms 357 are shown in FIG. 18 with ten electrodes 357 grouped in five electrode pairs 364 thereon. A flex strip (not shown) extends longitudinally through each of the arms, and electrodes 363 are formed on the flex strip. In addition, electrical or lead means in the form of conductors or traces 367 made from copper or any other suitable conductive material, a portion of one of which is shown in dashed lines in FIG. 18, are adhered to the flex strips and electrically connected to electrodes 363. Traces 367 extend from the electrodes to the proximal extremities 357a of the arms 357.

Means is disclosed in International Patent Application No. PCT/US96/18204 filed Nov. 13, 1996 for interconnecting proximal extremities 357a of arms 357 to distal extremity 352b of catheter shaft 352. In general, a cylindrical binder assembly or brace 371 is carried by distal extremity 352b for receiving the metal strips of arms 357. Proximal brace 371 is shown in dashed lines in FIG. 18 and is formed from a plurality of eight planar disks (not shown) made from stainless steel or any other suitable material. The metal strips of arms 357 extend through respective slots provided in the brace 371 and are precluded from being pulled out of the brace by tig welds formed on the proximal ends of the metal strips. The flex circuits within arms 357 extend along the outer cylindrical surface of brace 371 in circumferentially spaced-apart positions and terminate at a location proximal of the brace 371. Electrical or conductor means in the form of eight to ten conductor cables 372 are electrically connected by solder joints to traces 367 carried by the flex circuits. Cables 372 extend through catheter shaft 357 to proximal extremity 352a thereof.

Means which includes an a traumatic tip 376 is provided for interconnecting distal extremities 357b of arms 357 as more fully described in International Patent Application No. PCT/US96/18204 filed Nov. 13, 1996. Tip 376 includes a distal binder assembly or brace 377, shown in dash lines in FIG. 18, constructed from first and second plate members or disks (not shown) made from stainless steel or any other suitable material. The distal ends of the metal strips of arms 357 are secured to distal brace 377 in the same manner that the proximal ends of the metal strips are secured to proximal brace 371.

Handle means is coupled to proximal extremity 352a of catheter shaft 352 and includes a three-fold fitment 381 substantially similar to fitment 91. Fitment 381 has a central fitting 381a, a left fitting 381b and a right fitting 381c. Cables 372 extend through left fitting 381b to a connector 382 substantially similar to connector 143.

Medical probe 351 has push/pull means which includes a push/pull wire 386 for moving arms 357 from their predetermined shape shown in solid lines in FIG. 18 to a longitudinally-extended or contracted position, shown in phantom lines and identified by reference numeral 387 in FIG. 18, or to a fully bowed position showed in phantom lines in FIG. 18 and identified by reference numeral 388. Push/pull wire 386 has a proximal extremity 386a slidably disposed within passageway 354 of catheter shaft 352 and a distal extremity 386b connected to tip 376 by means of distal brace 377. As more fully described in International Patent Application No. PCT/US96/18204 filed Nov. 13, 1996, wire 386 has a sufficient column strength to withstand buckling when a compressive force is applied to the wire to push a traumatic tip 376 distally and thus move sector basket 356 to its extended position.

An additional flexible elongate tubular member 391 is slidably carried by push/pull wire 386. Tube member 391 is made from any suitable materials such as nylon, polyurethane or polyolefin and has proximal and distal extremities 391a and 391b. The tube member 391 has an external diameter ranging from three to four French. At least one and, as shown in FIG. 19, a plurality of lumens extend between extremities 391a and 391b. More specifically, a kidney-shaped central lumen 392 and two side lumens 393 and 394 extend between proximal and distal extremities 391a and 391b. Push/pull wire 386 is slidably disposed in first side lumen 393 and exits the lumen 393 where distal extremity 391b of tube member 391 joins proximal extremity 391a of the tube member 391. Tube proximal extremity 391a extends from central fitting 381a of fitment 381 to another three-fold fitment 397 having a central fitting 397a and left and right side fittings 397b and 397c. A strain relief tube 398 substantially similar to strain relief 137 is concentrically mounted about tube member 391 where it is secured to fitment 397.

The handle means of medical probe 351 includes a handle 401 of the type described in U.S. Pat. No. 5,478,330. Handle 401 has an elongate cylindrical body 402 and is provided with first finger actuatable means in the form of rotatable sleeve 403. Proximal extremity 386a of push/pull wire 386 extends from central fitting 397a of fitment 397 into handle body 402 where it couples to rotatable sleeve 403. Thus, rotation of sleeve 403 in a first angular direction about body 402 moves wire 386 proximally within passageway 354 to bow arms 357 outwardly from longitudinal axis 353. Conversely, rotation of sleeve 403 in an opposite second direction moves wire 386 distally within passageway 354 to collapse arms 357 of sector basket 356.

An electrode assembly 406 substantially similar to electrode assembly 256 is carried by the distal end of tube member 391. Like reference numerals have been used to describe like components of electrical assemblies 406 and 256. Electrode assembly 256 is mounted on the distal end of tube member distal extremity 391b and tube member proximal extremity 391a serves as means for slidably mounting distal extremity 391b on push/pull wire 386. The electrical assembly 406 includes, among other things, a large tip electrode 257 and a ring electrode 262. Electrodes 257 and 262 are diametrically sized larger than the external diameter of tube member distal extremity 391b and the internal diameter of catheter shaft passageway 354. First and second wires 276 and 277 and thermocouple wires 282 extend through central lumen 392 of tube member 391 and handle body 402. A cable 407 extends from handle body 402 and has a connector 408 secured to its free end. Wires 276 and 277 and thermocouple wires 272 are electrically coupled at their proximal ends to connector 408.

Electrode assembly 406 is cantilevered from push/pull wire 386 by distal extremity 391b of tube member 391. Distal extremity 391b extends from proximal extremity 391a substantially along longitudinal axis 353 as shown by the phantom lines in FIG. 18 when in its home or relaxed position. Distal extremity 391b of tube member 391 is flexible so as to be capable of being bent relative to longitudinal axis 353 and push/pull wire 386. Distal extremity 391b is shown in solid lines in FIG. 18 in one deflected position and more generally can be bent to an angle ranging from approximately 0° to 180° relative to the longitudinal axis 353, preferably to an angle ranging from 0° to 90° and more preferably to an angle of approximately 45° relative to axis 353. The distal extremity 391b has a length so that electrode assembly 406 extends outwardly beyond arms 357, at any position along the length of the mapping array, when distal extremity 391b is in a deflected position and sector basket 356 is in either an expanded or contracted position. More specifically, distal extremity or cantilever member 391 has a length ranging from 0.75 to 1.25 inch. The distal extremity 391b is thus spaced apart from wire 391 in FIG. 18 so as to engage the wall 148 of the heart when sector basket 356 is in an operationally bowed position within the chamber of the heart.

Pull wire means is carried by handle 401 for causing bending of distal extremity 391b. In this regard, an insulated pull wire 411 substantially similar to pull wire 287 extends from handle body 402 through fitment 337 and second side lumen 394 of tube member 391. The distal end of the pull wire 411 is secured to the inside of tip electrode 257 of electrode assembly 406. The proximal end of the pull wire 411 is coupled to knob 412 slidably mounted on handle body 402 which serves as the second finger actuatable means of handle 401. In the same manner as discussed above with respect to knob 273 of ablation catheter 246, proximal movement of knob 412 on body 402 exerts a tensile force on pull wire 411 which causes flexible distal extremity 391b to bend away from longitudinal axis 353. Distal extremity 391b of tube member 391 is provided with an internal spring member similar to ribbon 288 for returning distal extremity 391b to its straight position when a tensile force is no longer being exerted on pull wire 411.

Right fitting 381c of fitment 381 communicates with catheter shaft passageway 354 to permit a flushing fluid to be introduced through the passageway 354 and thus inhibit the formation of thrombus where tube member 391 exits passageway 354 at the distal end of catheter shaft 352. In a similar manner, left fitting 397b of fitment 397 communicates with first side lumen 393 of tube member 391 to permit a suitable flushing fluid to be introduced through the lumen 393 and inhibit the formation of thrombus where push/pull wire 386 exits the side of tube member 391. Right fitting 397c of fitment 397 communicates with central lumen 392 of tube member 391 to permit a saline or other cooling fluid to be introduced into internal chamber 261 of tip electrode 257 for cooling the electrode 257.

In operation and use, flexible cantilever member 391b extends along longitudinal axis 353 when introducing sector basket 356 and electrode assembly 406 into a chamber of the heart. Once the introducer catheter has been retracted relative to medical probe 351, basket arms 357 bow outwardly and cantilever member 391b can be deflected by knob 412 so as to extend sidewise of longitudinal axis 353. Electrode assembly 406 can be moved proximally and distally within sector basket 356 and along wire 386 by moving handle 401 rearwardly or forwardly relative to fitment 381. Rotation of handle 401 relative to the fitment 381 causes electrode assembly 406 to be rotated or swung about longitudinal axis 353 within the sector basket 356. In this manner, the electrode assembly 406 can be positioned within a space 358 between basket arms 357. Pull wire 411 and finger knob 412 further facilitate positioning of electrode assembly 406 within the heart by bending distal extremity 391b away from longitudinal axis 353.

Electrode assembly 406 can be used in the same manner as electrode assembly 256 to create deep lesions in the myocardium of the heart. Once the procedure has been completed, sector basket 356 and electrode assembly 406 can be withdrawn from the heart and body of the patient by means of the introducer catheter. Cantilever member 391b returns to its straightened position to permit its retraction into the introducer catheter and removal from the heart.

Medical probe 351 incorporates a movable electrode into a basket-like assembly having a central pull wire. The movable electrode is slidably mounted on the pull wire so that the pull wire and the movable electrode utilize the same lumen in the catheter shaft. Thus, a center steerable catheter can be placed into the central lumen of the basket-like assembly without losing any functionality of the pull wire.

Other electrode assemblies can be mounted on the distal end of tube member 391 and be within the scope of the present invention. For example, such electrode assemblies having electrodes smaller or larger than tip electrode 257 can be provided. It should be further appreciated that any of the movable or slidable electrodes disclosed herein can be matched with any of the various basket-like assemblies disclosed herein and be within the scope of the present invention. Further, any of such movable electrodes that are slidably mounted on an elongate member can be slidably mounted on any of the various mapping or support arms of any of such basket-like assemblies disclosed herein.

Figures 20, 21:
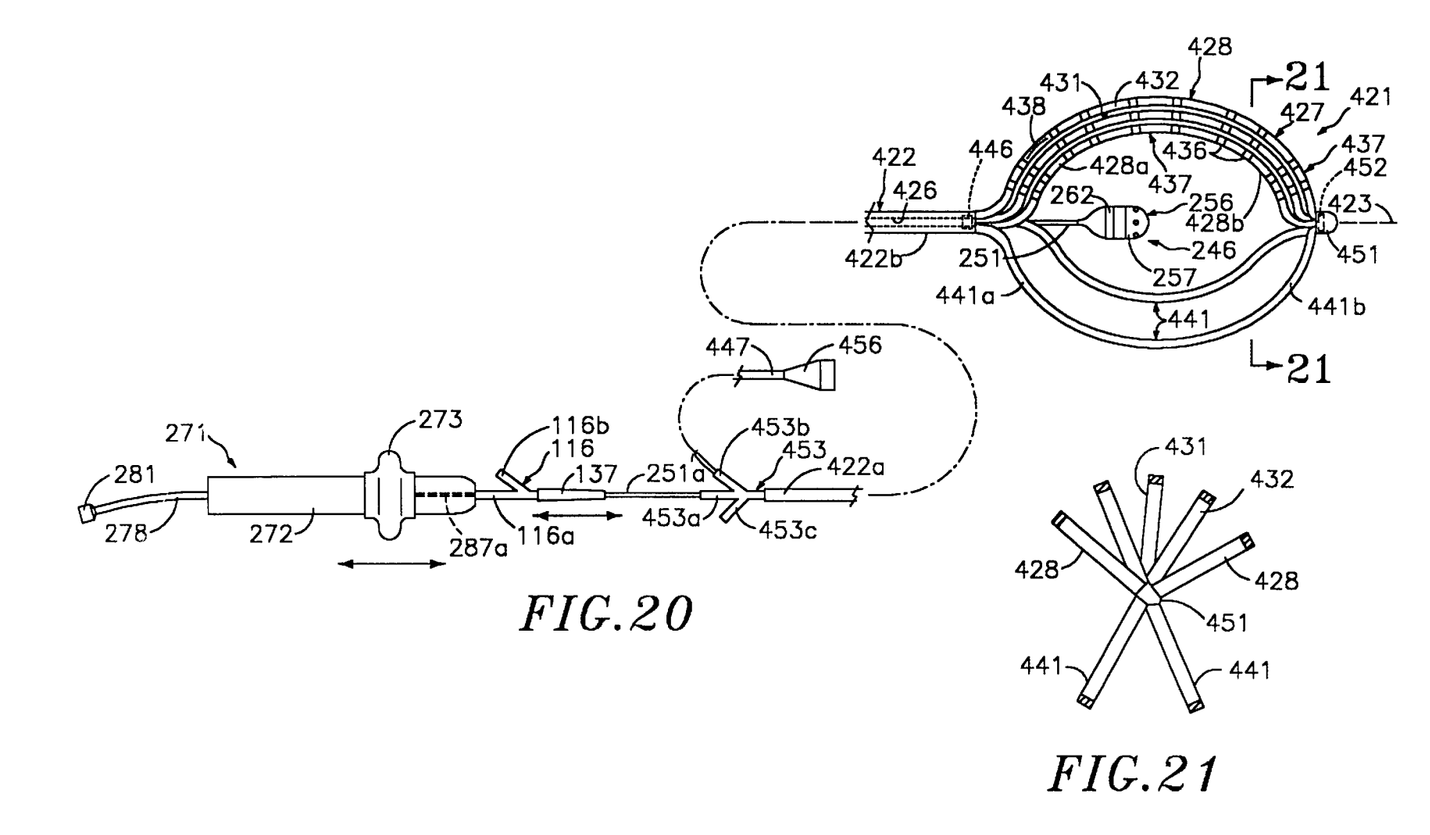
FIG. 20 is a side elevational view of another embodiment of the endocardial mapping catheter with movable electrode of the present invention.
FIG. 21 is a cross-sectional view of the endocardial mapping catheter of FIG. 20 taken along the line 21—21 of FIG. 20.

Another embodiment of an endocardial mapping catheter with a movable electrode is disclosed in FIGS. 19–20. Endocardial mapping catheter or medical probe 421 is of the type described in International Patent Application No. PCT/US96/18204 filed Nov. 13, 1996. Medical probe 421 has a flexible elongate tubular member or catheter shaft 422 made from any suitable material such as plastic. Catheter shaft 422 has proximal and distal extremities 422a and 422b and extends along a central longitudinal axis 423. The shaft 422 has an external diameter of approximately nine French. At least one lumen or passageway 426 extends between the proximal and distal extremities 422a and 422b parallel to axis 423.

An expandable means in the form of a basket-like assembly or sector-shaped basket 427 is carried by distal extremity 422b. Sector-shaped or sector basket 427 has a longitudinal dimension smaller than the longitudinal dimension of the heart chamber in which it is to be used and is formed from a plurality of longitudinally-extending spaced-apart members which include five longitudinally-extending spaced-apart arms 428 having proximal and distal extremities 428a and 428b. Mapping arms 428 are movable between a first or contracted position in which the arms collapse and extend generally along longitudinal axis 423 and a second or expanded position in which the arms bow outwardly along one side of longitudinal axis 423. Arms 428, which are shown in an expanded position FIGS. 20 and 21, are asymmetrically spaced relatively close together along longitudinal axis 423 in a group, as shown in FIG. 21. The arms 428 are asymmetrically spaced about or around axis 423 and subtend an angle ranging from approximately 60° to 180° about the axis and, more specifically, an angle of approximately 120° about the axis. As such, adjacent arms 428 are angularly spaced apart by an angle of approximately 30°. Spaces 431 are provided between adjacent arms 428.

Each of arms 428 is generally strip-like in conformation and has opposite outer and inner planar surfaces 432. Each of arms 428 has a predetermined bowed shape, shown in FIG. 20, provided by a spring-like support member or strip (not shown) extending longitudinally therethrough and preferably made from a superelastic shape memory alloy such as Nitinol. A plurality of electrodes 436 are carried by sector basket or basket-like assembly 427 in longitudinally and radially spaced-apart positions on the basket. More specifically, eight to ten electrodes 436 are carried by each arm 428 and the electrodes 436 on each arm are grouped into four to five pairs so as to provide a plurality of four to five longitudinally spaced-apart electrode pairs 437 on each of the arms. The basket arms 438 are shown in FIG. 20 with ten electrodes 436 grouped into five electrode pairs 437 thereon. A flex strip (not shown) extends longitudinally through each of the arms and electrodes 436 are formed on the flex strip. In addition, electrical or leads means in the form of conductors or traces 438, made from copper or any other suitable conductive material, are adhered to the flex strips and electrically connected to electrodes 436. Traces 438 extend from the electrodes to the proximal extremities 428a of the arms 428.

Sector basket 427 further includes two additional longitudinally-extending spaced-apart members or support arms 441 movable between a first or contracted position in which the arms 441 collapse and extend generally along longitudinal axis 423 and a second or expanded position in which the arms 441 bow outwardly along the side of axis 423 opposite mapping arms 428. Support arms 441 have proximal and distal extremities 441*a* and 441*b* and have a flexible metal spring-like support member or strip (not shown) extending longitudinally therethrough and preferably made from a superelastic shape memory alloy such as Nitinol. An insulating sleeve (not shown) encapsulates the metal strip and forms the outer surface of each of the support arms 441.

Means is disclosed in International Patent Application No. PCT/US96/18204 filed Nov. 13, 1996 for interconnecting proximal extremities 428*a* of mapping arms 428 and proximal extremities 441*a* of support arms 441 to distal extremity 422*b* of catheter shaft 422. In general, a cylindrical binder assembly or brace 446 is carried by distal extremity 422*b* for receiving the metal strips of arms 428 and 441. Proximal brace 446 is shown in dashed lines in FIG. 20 and is formed from a plurality of eight planar disks (not shown) made from stainless steel or any other suitable material. The metal strips of mapping arms 428 and support arms 441 extend through respective slots provided in the brace 446 and are precluded from being pulled out of the brace by tig wells formed on the proximal ends of the metal strips. The flex circuits within mapping arms 428 extend along the outer cylindrical surface of brace 446 in circumferentially spaced-apart positions and terminate at a location proximal of the brace 446. Electrical or conductor means in the form of eight to ten conductor cables 447 are electrically connected by solder joints to traces 438 carried by the flex circuits. Cables 447 extend through catheter shaft 422 to proximal extremity 422*a* thereof.

Means which includes an a traumatic tip 451 is provided for interconnecting distal extremities 428*b* of mapping arms 428 and distal extremities 441 of support arms 441. A traumatic tip 451, as more fully described in International Patent Application No. PCT/US96/18204 filed Nov. 13, 1996, includes a distal binder assembly or brace 452 which is shown in dashed lines in FIG. 20. Brace 452 is constructed from first and second plate members for disks (not shown) made from stainless steel or any other suitable material. The distal ends of the metal strips in mapping and support arms 428 and 441 are secured to distal brace 452 in the same manner that the proximal ends of the metal strips are secured to proximal brace 446.

Handle means is coupled to proximal extremity 422*a* of catheter shaft 422 and includes a three-fold fitment 453 substantially similar to fitment 91. Fitment 453 has a central fitting 453*a*, a left fitting 453*b* and a right fitting 453*c*. Cables 447 extend through left fitting 453*b* to a connector 456 substantially similar to connector 143.

Ablation catheter 246 described above and illustrated in FIGS. 11–13 is integrally coupled with medical probe 421 in the same manner in which catheter 246 is described above as being integrally coupled with medical probe 247. Like reference numerals have been used in FIG. 20 to describe like components in FIGS. 20 and in FIGS. 11–13. Specifically, catheter shaft 251 of ablation catheter 246 is slidably disposed in central passageway 426 of catheter shaft 422. The central passageway 42E has an internal diameter slightly larger than the external diameter of catheter shaft 251 to permit such slidable movement. Electrode assembly 256 is carried by distal extremity 422*b* of catheter shaft 422 and is permanently disposed within sector basket 427. In this regard, tip electrode 257 has an external diameter which is larger than the external diameter of catheter shaft 251, as discussed above, and is larger than the internal diameter of passageway 426. The handle means of medical probe 421 includes handle 271. It should be appreciated that ablation catheter 301 could also be integrally coupled to medical probe 247 and be within the scope of the present invention.

In operation and use, sector basket 427 can be introduced into a chamber of the heart such as the left ventricle in the manner discussed above to perform high density mapping of the endocardium. As more fully described in International Patent Application No. PCT/US96/18204 filed Nov. 13, 1996, mapping arms 428 are urged against the heart wall by oppositely aligned support arms 441 to permit electrode pairs 437 to perform high density mapping of a selected portion of the endocardium. Sector basket 427 can be moved longitudinally within the heart chamber and rotated within the heart chamber to desirably position electrodes 436 on the endocardium. Electrodes 436 can also be used to ablate the heart wall. Electrode assembly 256 can be used to further map the heart wall and to create a relatively large lesson in the myocardium. In this regard, electrode assembly 256 can be steered by means of handle 271 so as to engage the heart wall in spaces 431 between mapping arms 428 or otherwise around the mapping arms or within sector basket 427. Tip electrode 257 can be used with ring electrode 262 to determine the location of electrode assembly 256 on the heart wall. Radio frequency energy is provided to tip electrode 257 for ablating the heart wall.

From the foregoing, it can be seen that a new and improved endocardial mapping catheter with a movable electrode has been provided. The movable electrode can be an ablation electrode carried within a basket-like assembly and having a diameter which is large relative to the diameter of the catheter shaft on which the ablation electrode is mounted. Such an ablation electrode has a diameter which is large relative to the diameter of the lumen in the catheter shaft of the basket-like assembly in which the ablation catheter shaft is disposed Alternatively, the movable electrode can be a saline electrode. The movable electrode can be slidably disposed on a basket-like assembly as, for example, an arm rotatably mounted within the basket-like assembly or a pull wire of a basket-like assembly. The movable electrode can be cantilevered from the pull wire so as to be positionable between the arms of the basket-like assembly. In addition, the movable electrode can be directed in first and second opposite directions by means of a push/pull wire.

What is claimed is:

1. In an endocardial mapping catheter for introduction into a chamber of a heart formed by a wall, a flexible elongate tubular member having proximal and distal extremities and extending along a longitudinal axis, a plurality of longitudinally-extending arms carried by the distal extremity of the flexible elongate tubular member and having proximal and distal extremities, proximal means interconnecting the proximal extremities of the arms and distal means interconnecting the distal extremities of the arms, the arms being movable between contracted positions and expanded positions in which the arms bow outwardly from the longitudinal axis, the arms having spaces therebetween when in the expanded positions, a plurality of longitudinally spaced-apart electrodes carried by each of the arms, electrical means extending through the flexible elongate tubular member and connected to the electrodes for performing electrical functions with respect to the electrodes, a large ablation tip electrode having a diameter of at least five French and means carried by the flexible elongate tubular member and secured to the large ablation tip electrode for moving the large ablation tip electrode between a first position close to the longitudinal axis and a second position away from the longitudinal axis into a space between the arms for engaging the wall of the heart and creating lesions in the wall of the heart.

2. A catheter as in claim 1 wherein the arms subtend an angle of 180° or less about the longitudinal axis to form a sector-shaped basket.

3. A catheter as in claim 1 wherein the means carried by the flexible elongate tubular member for moving the large ablation tip electrode between a first position close to the longitudinal axis and a second position away from the longitudinal axis into a space between the arms includes an elongate flexible member carried within the flexible elongate tubular member and secured to the large ablation tip electrode.

4. A catheter as in claim 3 together with means carried by the proximal extremity of the flexible elongate tubular member for rotating the elongate flexible member within the flexible elongate tubular member.

5. A catheter as in claim 3 wherein the distal extremity of the flexible elongate tubular member is provided with a lumen, at least a portion of the elongate flexible member being slidably disposed in the lumen.

6. A catheter as in claim 3 wherein the large ablation tip electrode is made from a conductive metal, the conductive metal forming an internal chamber and the elongate flexible member being provided with a lumen in communication with the chamber for supplying a cooling liquid to the chamber.

7. A catheter as in claim 1 together with a ring electrode mounted on the distal extremity of the elongate tubular member proximal of the large ablation tip electrode.

8. A catheter as in claim 1 wherein the large ablation tip electrode has a surface area ranging from approximately 10 to 40 mm$^2$.

9. A catheter as in claim 1 wherein the large ablation tip electrode has a diameter ranging from six to seven French.

10. In an endocardial mapping catheter for introduction into a chamber of a heart formed by a wall, a flexible elongate tubular member extending along a longitudinal axis, the flexible elongate tubular member having proximal and distal extremities and provided with a lumen extending from the proximal extremity to the distal extremity, the lumen having an internal diameter, a plurality of longitudinally-extending arms carried by the distal extremity of the flexible elongate tubular member and having proximal and distal extremities, proximal means interconnecting the proximal extremities of the arms and distal means interconnecting the distal extremities of the arms, the arms being movable between contracted positions and expanded positions in which the arms bow outwardly from the longitudinal axis, the arms having spaces therebetween when in the expanded positions, a plurality of longitudinally spaced-apart electrodes carried by each of the arms, electrical means extending through the flexible elongate tubular member and connected to the electrodes for performing electrical functions with respect to the electrodes, an elongate flexible member slidably disposed in the lumen of the flexible elongate tubular member, the elongate flexible member having an external diameter and a distal extremity, a large ablation electrode mounted on the distal extremity of the elongate flexible member, the large ablation electrode having an external diameter greater than the external diameter of the elongate flexible member and greater than the internal diameter of the lumen of the flexible elongate tubular member, the large ablation electrode movable by the elongate flexible member into a space between the arms for engaging the wall of the heart and creating lesions in the wall of the heart.

11. A catheter as in claim 10 wherein the large ablation electrode has an external diameter of at least five French.

12. A catheter as in claim 10 wherein the elongate flexible member has a pull element for deflecting the distal extremity of the elongate flexible member.

13. A catheter as in claim 12 wherein the elongate flexible member has means for returning the elongate flexible member to a substantially straightened position after the elongate flexible member has been deflected by the pull element.

14. A catheter as in claim 12 wherein the pull element is included within means for returning the elongate flexible member to a substantially straightened position, support means extending the length of the pull element for inhibiting the pull element from buckling when a compressive force is exerted on the pull element.

* * * * *